United States Patent
Kohno et al.

(10) Patent No.: US 10,213,097 B2
(45) Date of Patent: Feb. 26, 2019

(54) ENDOSCOPE

(71) Applicant: Panasonic Intellectual Property Management Co., Ltd., Osaka (JP)

(72) Inventors: Haruhiko Kohno, Fukuoka (JP); Yuichi Hatase, Fukuoka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 127 days.

(21) Appl. No.: 14/882,231

(22) Filed: Oct. 13, 2015

(65) Prior Publication Data

US 2016/0100748 A1 Apr. 14, 2016

(30) Foreign Application Priority Data

Oct. 14, 2014 (JP) ................. 2014-209743

(51) Int. Cl.
| | | |
|---|---|---|
| *A62B 1/04* | (2006.01) | |
| *A61B 1/045* | (2006.01) | |
| *A61B 1/00* | (2006.01) | |
| *A61B 1/12* | (2006.01) | |
| *A61B 1/05* | (2006.01) | |
| *A61B 1/005* | (2006.01) | |
| *H04N 5/225* | (2006.01) | |

(52) U.S. Cl.
CPC .......... *A61B 1/045* (2013.01); *A61B 1/00009* (2013.01); *A61B 1/00018* (2013.01); *A61B 1/00071* (2013.01); *A61B 1/05* (2013.01); *A61B 1/128* (2013.01); *A61B 1/0055* (2013.01); *A61B 1/0057* (2013.01); *H04N 2005/2255* (2013.01)

(58) Field of Classification Search
CPC ........... A61B 1/00009; A61B 1/00018; A61B 1/00071; A61B 1/045; A61B 1/05; A61B 1/128; A61B 1/0055; A61B 1/0057; H04N 2005/2255
See application file for complete search history.

(56) References Cited

U.S. PATENT DOCUMENTS

| | | | | |
|---|---|---|---|---|
| 5,315,383 A | * | 5/1994 | Yabe | ...... A61B 1/042 348/68 |
| 2004/0220453 A1 | * | 11/2004 | Jones | ...... A61B 1/00096 600/160 |
| 2013/0012777 A1 | * | 1/2013 | Baum | ...... A61B 1/00013 600/110 |
| 2013/0035552 A1 | * | 2/2013 | Moriyama | ...... A61B 1/00073 600/149 |

(Continued)

FOREIGN PATENT DOCUMENTS

| | | |
|---|---|---|
| JP | 07-327916 A | 12/1995 |
| JP | 2012-050704 A | 3/2012 |
| JP | 2014-103151 A | 6/2014 |

*Primary Examiner* — Dakshesh D Parikh
*Assistant Examiner* — Peet Dhillon
(74) *Attorney, Agent, or Firm* — Seed IP Law Group LLP

(57) ABSTRACT

An endoscope has an imaging unit at a distal end portion of an insert section, and a relay board including an imaging signal converter that converts imaging signals output from the imaging unit is provided inside the insert section. Here, a data transmission method of an imaging signal transmitted at least in a section from the imaging unit to the relay board is a low-amplitude differential transmission method.

7 Claims, 6 Drawing Sheets

(56) References Cited

U.S. PATENT DOCUMENTS

2013/0286173 A1* 10/2013 Doi .................... A61B 1/00181
348/65
2015/0088001 A1* 3/2015 Lindvold ........... A61B 1/00186
600/478

* cited by examiner

ENDOSCOPE

BACKGROUND OF THE INVENTION

1. Field of the Invention

The present invention relates to an endoscope, and particularly, to a small-sized endoscope that performs observation, surgery, or the like of a constricted part in the medical field or the industrial field.

2. Description of the Related Art

In the related art, in the medical field or the industrial field, endoscopes for imaging the interior of a patient's body or the inside of a device or a structure have spread. In these types of endoscopes, there is known a configuration in which, in an insert section inserted into the inside of an object to be observed, the light from an object to be imaged is image-formed on a light-receiving surface of an image pickup device by an objective lens systems, and the image-formed light is converted into electrical signals and the converted electrical signals are transmitted to an external image processing device or the like as video signals via a signal cable.

A number of parts, such as optical elements, such as an image pickup device and a lens that focuses a light image on an imaging surface of the image pickup device, are arranged in a distal end portion provided at the distal end of the insert section of these types of endoscopes. There is known a configuration in which an imaging direction, that is, a visual field, is changed on the basis of the operation of a surgeon or the like by connecting the distal end portion to a linear hard part on a rear end side of the insert section via a bendable bending portion. In recent years, in the endoscopes having a complicated configuration in this way, in order to perform simpler manufacturing and to alleviate a patient's burden, further diameter reduction of the external diameter has been important.

For example, Japanese Patent Unexamined Publication No. 7-327916 discloses a visual-field direction change type endoscope that includes visual-field conversion means that causes some of rays, which are incident from a transparent window arranged from a distal end surface of a distal end of an insert section to the middle of a side portion near the distal end, to selectively enter an objective optical system of a rotationally provided imaging unit and to fall within a visual field range, and that can freely switch the direction of the visual field of the endoscope according to the applications thereof or an object to be observed.

Japanese Patent Unexamined Publication No. 2012-50704 discloses an electronic endoscope in which a space for installing an imaging module including an image pickup device is provided inside a distal end portion of the endoscope, the inside of a metal frame including the imaging module is filled with isotropic high heat conduction resin, and a space around the metal frame is filled with anisotropic high heat conduction resin having a higher thermal conductivity in the direction of an outer peripheral portion of the endoscope than that in a longitudinal direction of the endoscope.

In the endoscope having the configuration in which the imaging unit including the image pickup device is arranged at the distal end portion as described above, a countermeasure against dissipation of the heat generated in the image pickup device becomes a challenge. Particularly when the endoscopes are used in the medical field, heat dissipation of a distal end portion is required in order to suppress the temperature of the endoscope insert section within a human's body that is a photographic subject with the suppression of performance deterioration, such as an increase in noise caused by heat generation.

When a low-resolution image pickup device is used, heat is not generated so much. Therefore, this does not become a problem. However, when a high-resolution image pickup device is used, the heat generation in the image pickup device is large in the related art. Therefore, a heat dissipation structure of the distal end portion is required. In the endoscope including the high heat conduction resin and a tubular body as the heat dissipation structure of the distal end portion in which the imaging unit is arranged as in the related-art example described in Japanese Patent Unexamined Publication No. 2012-50704, the diameter of the distal end portion becomes large, and there is a problem in that bending becomes difficult.

SUMMARY OF THE INVENTION

An object of the invention is to provide an endoscope that can suppress heat generation in a distal end portion of an insert section while achieving downsizing of the distal end portion of the insert section in view of the above circumstances.

An endoscope related to the invention includes an imaging unit provided at a distal end portion of an insert section; and an imaging signal converter provided inside the insert section to convert an imaging signal output from the imaging unit.

According to the invention, in the endoscope, the heat generation in the distal end portion of the insert section can be suppressed while achieving downsizing of the distal end portion of the insert section.

DETAILED DESCRIPTION OF THE PREFERRED EMBODIMENTS

Figure 1:
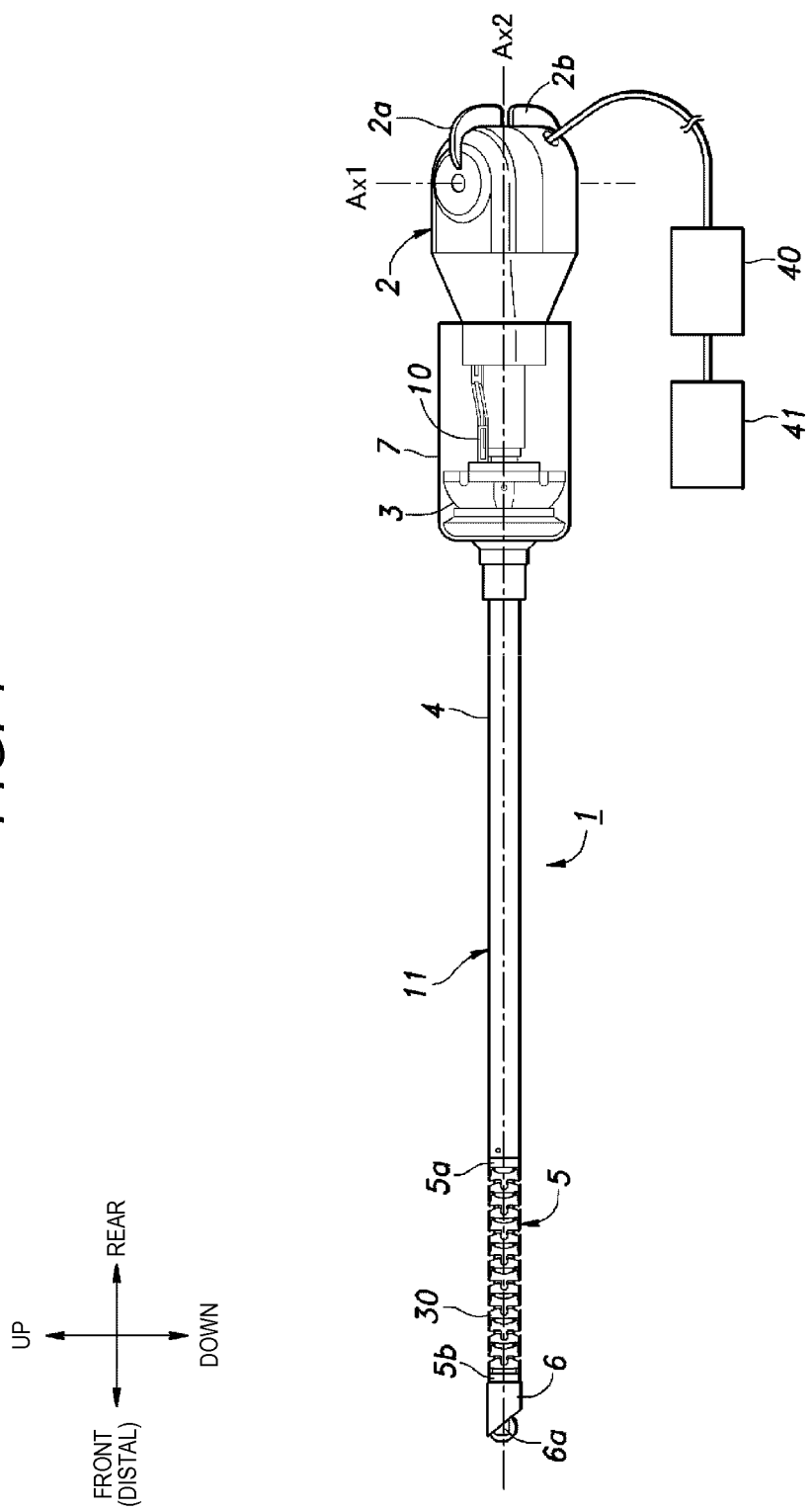
FIG. 1 is an overall configuration view of an endoscope related to the present embodiment.

Hereinafter, embodiments related to the invention will be described referring to the drawings. Directions used for explanation follow the description of directions in the respective drawings in principle. It should be noted herein that a direction in which members formed in a tubular shape or a rod shape extend or the direction of a rotation axis of rotating members may be referred to as an "axial direction". An inward or outward direction with an axis as a center may be referred to as a "radial direction" or a rotating direction with an axis as a center may be referred to as a "circumferential direction". Regarding members in which a section orthogonal to the axial direction has a rectangular shape, the above directions may also be referred to as the "radial direction" and the "circumferential direction" for convenience.

FIG. 1 is an overall configuration view of endoscope 1 related to the present embodiment. In the present embodiment, an endoscope used for surgery of the abdomen or the like of a human body in the medical field is taken as an example, and the configuration thereof is illustrated.

Endoscope 1 mainly has grip section 2, connection part 3, and insert section 11 inserted into a part to be observed. Insert section 11 has, from the base end side, hard part 4 that is connected to grip section 2 via connection part 3, has a linear pipe shape, and is incapable of being bent, bending portion 5 configured to be bendable, and distal end portion 6 in which imaging unit 6a that functions as an imaging unit is housed. An outer peripheral portion of connection part 3 is provided with a rotation operating section 7 that is rotated with an extending direction of hard part 4 as a center.

When surgery under a laparoscope is performed using endoscope 1, distal end portion 6 and bending portion 5 of insert section 11 are guided to a surgery part via a trocar or a trocar tube. Meanwhile, a portion of hard part 4 of insert section 11 on the base end side is brought into the state of coming out of the body, and surgery is conducted while a surgeon or the like grips grip section 2 and performs an operation.

Grip section 2 is provided with first operation section 2a that performs an operation in order to bend bending portion 5, and second operation section 2b that operates an imaging direction based on imaging unit 6a mounted on distal end portion 6. In grip section 2, first operation section 2a and second operation section 2b are rotatable about first axis Ax1 that is a rotation axis of each operation section.

If the surgeon or the like operates first operation section 2a, bending portion 5 is bent toward a predetermined direction (for example, downward in the drawing) according to the amount of operation thereof, and the imaging direction of imaging unit 6a provided in distal end portion 6 changes, that is, the visual field thereof moves. In this case, in consideration of operability, a configuration is adopted such that the rotational direction of first operation section 2a and the bending direction of bending portion 5 are configured to coincide with each other.

If the surgeon or the like operates second operation section 2b, imaging unit 6a pivotally supported within distal end portion 6 rotates, and the imaging direction of imaging unit 6a changes, that is, the visual field thereof moves. Here, the visual field of imaging unit 6a moves between the front side and the lower side in the drawing.

In the subsequent description, an operation in which bending portion 5 is bent by the operation of first operation section 2a, and thereby, the visual field is moved may be referred to as "bending operation", an angle formed by a direction in which the distal end of distal end portion 6 is pointed by bending and a central axis direction (second axis Ax2) of hard part 4 may be referred to as a "bending angle", and a direction in which the distal end of distal end portion 6 is pointed by bending in a front view may be referred to as a "bending direction". For example, the bending portion 5 being bent such that the distal end of distal end portion 6 is pointed downward (upward) in the drawing may be expressed like "being bent downward (upward)".

In the subsequent description, an operation in which the visual field of imaging unit 6a is moved by operating second operation section 2b is referred to as "tilting operation" or simply "tilting". The operation ranges (rotational ranges centered on first axis Ax1) of first operation section 2a and second operation section 2b are regulated by a stopper (not illustrated) provided at grip section 2. First operation section 2a and second operation section 2b may adopt a configuration using a rotary grip or the like other than a lever type as illustrated.

FIG. 1 illustrates an initial state of endoscope 1. In this case, bending portion 5 is linear, and the visual field of imaging unit 6a in distal end portion 6 is pointed forward in the drawing. From this state, if first operation section 2a is operated, bending portion 5 is bent downward in the drawing, and if second operation section 2b is operated, imaging unit 6a is tilted downward in the drawing.

Figure 2:
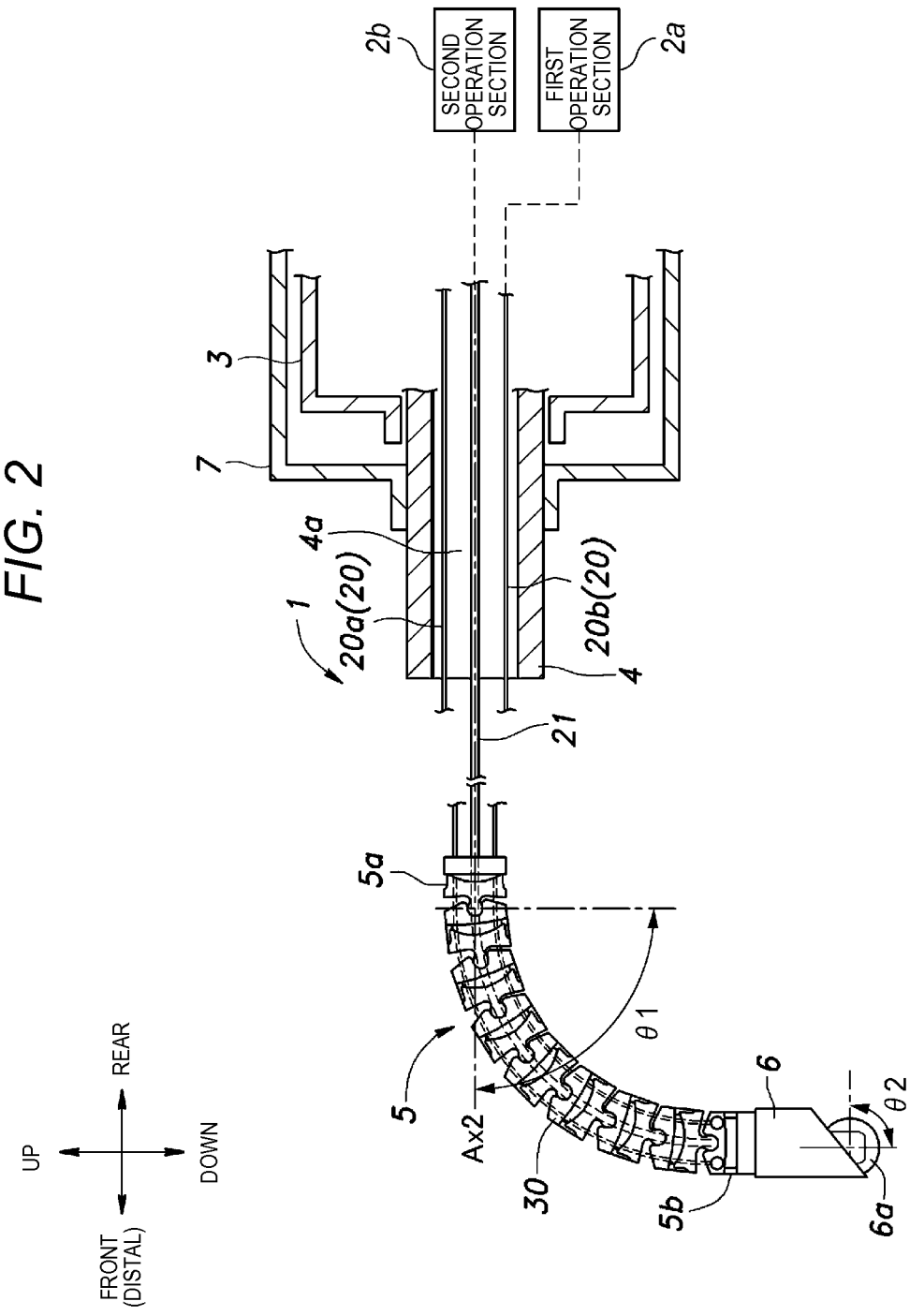
FIG. 2 is an explanatory view illustrating the bending operation of a bending portion and the tilting operation of an imaging unit within a distal end portion.

FIG. 2 is an explanatory view illustrating the bending operation of bending portion 5 and the tilting operation of imaging unit 6a within distal end portion 6. FIG. 2 illustrates a state where bending portion 5 is bent downward in the drawing.

Bending portion 5 extends from base end 5a to free end 5b, and is configured to have a plurality of joint pieces 30 that are rotatably connected together between base end 5a and free end 5b. In the subsequent description, an axis that an assembly of the plurality of joint pieces 30 constitutes may be referred to as an "axis of bending portion 5" and the direction of the axis may be referred to as an "axial direction of bending portion 5". Since bending portion 5 is bendable, the "axial direction of bending portion 5" varies according to the bending direction and the bending angle.

Joint pieces 30 are members that are made of, for example, stainless steel, and form a rectangular shape having rounded corners or a circular shape as seen from the axial direction of bending portion 5. By connecting a plurality of joint pieces 30 together so as to shift from each other every 90 degrees alternately in the circumferential direction, free end 5b of bending portion 5 is configured to be bendable in the arbitrary directions with respect to base end 5a. Bending portion 5 is bent inside the plurality of joint pieces 30 by inserting control wires 20 (first control wire 20a and second control wire 20b), pulling one of control wires 20, and loosening the other control wire.

Hard part 4 is a tubular linear member having hollow portion 4a extending in the direction of second axis Ax2, and is made of, for example, stainless steel. Hard part 4 has base end 5a of bending portion 5 attached to one end thereof on the distal end side and has the other end on the base end side connected to grip section 2 via connection part 3, and extends forward from grip section 2.

Connection part 3 is supported by grip section 2 on the base end side (on the rear side in the drawing) thereof, and is connected to hard part 4 on the front side thereof. Connection part 3 and grip section 2 are connected together by link member 10 (refer to FIG. 1). An operating force generated by the operation of first operation section 2a is transmitted to connection part 3 by link member 10. Control wires 20 are inserted through the insert section ranging from connection part 3 to hard part 4 and bending portion 5, and are provided to be movable through the insert section. In connection part 3, the operating force of first operation section 2a is converted into pulling forces of control wires 20, and is transmitted to free end 5b of bending portion 5 on the distal end side.

Spring joint 21 is inserted through the insert section ranging from grip section 2 through connection part 3 to hard part 4 and bending portion 5, and is rotatably provided therein. An operating force generated by the operation of second operation section 2b is converted into a rotary force of spring joint 21 centered on second axis Ax2 by a gear mechanism provided inside grip section 2, and this rotary force is transmitted to distal end portion 6 of the insert section. The rotary force of spring joint 21 is converted into a linear motion from a rotational motion by a connection mechanism provided inside distal end portion 6, and a drive arm (not illustrated) moves in a forward-rearward direction (a longitudinal direction of insert section 11).

Since imaging unit 6a has both side portions rotatably supported in distal end portion 6 and is connected to the drive arm, the imaging unit 6a is rotated (tilted) about a supporting shaft pivotally supported within distal end portion 6 with the movement of the drive arm in the forward-rearward direction, and the visual field thereof moves.

In the example of FIG. 2, the bending angle of bending portion 5 is θ1 (for example, 0° to 90°), and the tilting angle of imaging unit 6a is θ2 (for example, 0° to 90°). By combining the above-described bending operation and tilting operation, the direction of the visual field of imaging unit 6a varies by an angle θ1+θ2. Hence, it is also possible to increase the movement range of the visual field to 0° to 180° without increasing the bending angle of bending portion 5, (that is, without occupying a large space in bending). In endoscope 1 of the present embodiment, the movement angle of the visual field is added together by the combination of the bending operation in which bending portion 5 that is linear in an initial state is bent, and the tilting operation in which the imaging unit itself pivotally supported within distal end portion 6 is rotated.

In the present embodiment, as illustrated in FIG. 1, a state where bending portion 5 is not bent is brought into the initial state. However, the invention is not limited to this. For example, a configuration may be adopted in which an arbitrary state is brought into the initial state, such as bringing a state where bending portion 5 is bent upward as the initial state, and the bending operation and the tilting operation are performed at a predetermined bending angle and at a predetermined tilting angle such that the visual field is displaced.

Operation wires 20 that bend bending portion 5 only have to be provided in an arbitrary number according to the bending direction. Although a configuration example in which bending portion 5 formed by connecting plurality of joint pieces 30 together is bent by control wires 20 that pull and loosen bending portion 5 is illustrated as a bending mechanism, the bending mechanism is not limited to this. Although an example in which imaging unit 6a itself is configured so as to be rotated around the pivotally supported shaft is illustrated as a tilting mechanism, the tilting mechanism is not limited to this. For example, a configuration may be adopted in which the image pickup device is fixed in distal end portion 6, and an optical member, such as a mirror member, which is provided between the image pickup device and the optical lens, is rotated so as to change a light path of photographic subject light.

Imaging unit 6a has an image pickup device (not illustrated) constituted of a small Charge Coupled Device (CCD), a small-sized Complementary Metal-oxide Semiconductor (CMOS) or the like, and an optical lens (not illustrated) that focuses entered photographic subject light on the image pickup device. Imaging unit 6a having such a shape can be realized by applying a camera module used for, for example, a smart phone or a tablet terminal to other purposes.

Endoscope 1 is connected to video processor 40 and display unit 41 via a cable from grip section 2. Image signals of a still image or a moving image obtained by imaging an object to be observed (here, the inside of a human body), using imaging unit 6a of distal end portion 6, are transmitted to video processor 40, and are subjected to various kinds of signal processing or the like in video processor 40. The image of the object to be observed and processed by video processor 40 is displayed on display unit 41. Meanwhile, endoscope 1 is operated by receiving electric power and various control signals from video processor 40, and imaging is performed at timings based on the control signals in imaging unit 6a.

Figure 3:
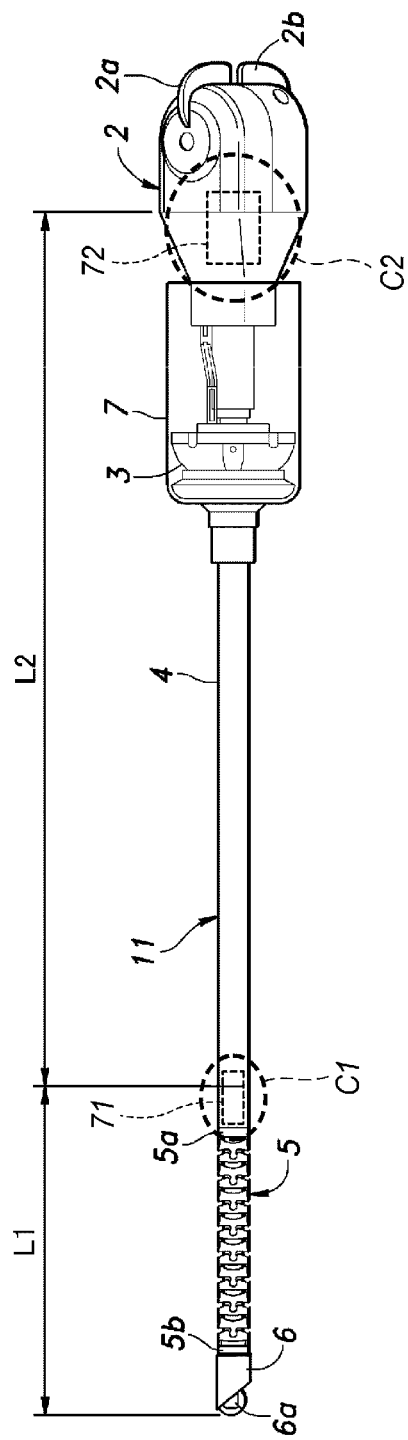
FIG. 3 is a view illustrating an arrangement configuration of boards provided within an insert section.
Figure 4:
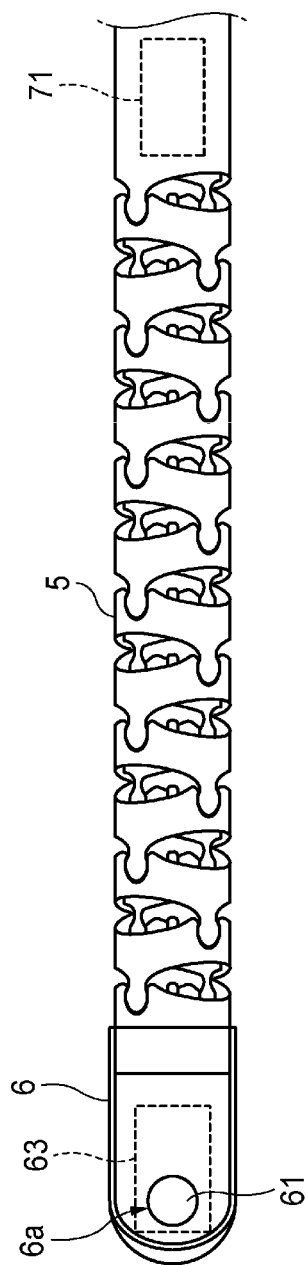
FIG. 4 is a view illustrating the arrangement configuration of the boards in the distal end portion and the bending portion.
Figure 5:
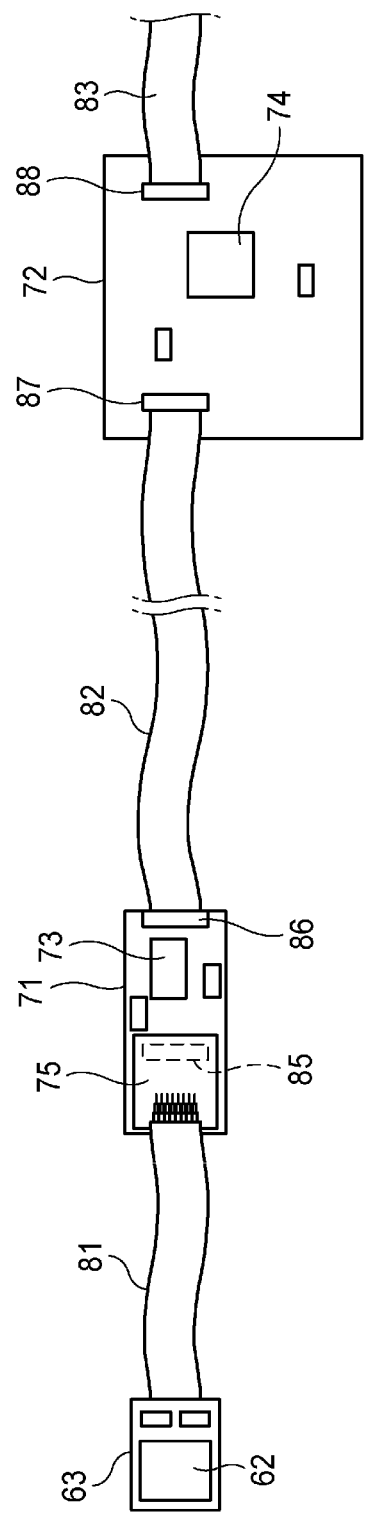
FIG. 5 is a view illustrating a specific configuration example of the boards and cables.

Next, the configuration of cables and boards that are provided inside endoscope 1 will be described with reference to FIGS. 3, 4, and 5. FIG. 3 is a view illustrating an arrangement configuration of boards provided within insert section 11, FIG. 4 is a view illustrating the arrangement configuration of the boards in distal end portion 6 and bending portion 5, and FIG. 5 is a view illustrating a specific configuration example of the boards and cables.

In the present embodiment, as for the dimensions of insert section 11 of endoscope 1, for example, length L1 from imaging unit 6a of distal end portion 6 to the portion (distal end portion of hard part 4) of bending portion 5 on the rear end side is about 100 mm, and length L2 from distal end portion of hard part 4 to grip section 2 is about 600 mm. Hereinafter, a distal end portion of hard part 4 is referred to as intermediate portion C1, and a portion of grip section 2 is referred to as base end portion C2. The external diameter of distal end portion 6, bending portion 5, and hard part 4 is about 10 mm at the maximum portion.

Inside insert section 11, a configuration is adopted in which relay board 71 is provided at intermediate portion C1, image output board 72 is provided at base end portion C2, and imaging signals of a photographic subject captured by imaging unit 6a are relayed in relay board 71.

Imaging unit 6a of distal end portion 6 has optical lens 61 that focuses a photographic subject image, image pickup device 62, such as a CCD or a CMOS, and image board 63 on which image pickup device 62 is mounted, and image board 63 is arranged within distal end portion 6. Relay board 71 on which a signal conversion circuit for relaying imaging signals is mounted is arranged at intermediate portion C1 in the distal end portion of hard part 4, and image board 63 and relay board 71 are connected to each other by first cable 81. Image output board 72 on which an image output circuit for outputting imaging signals to video processor 40 is mounted is arranged at base end portion C2 in grip section 2, and relay board 71 and image output board 72 are connected to each other by second cable 82.

Image board 63 has, for example, a size of about 5 mm×6 mm, has image pickup device 62 mounted on one surface thereof, and has one end of first cable 81 connected thereto by soldering or the like. First cable 81 is inserted through bending portion 5, and transmits imaging signals output from imaging unit 6a and electric power and control signals to be supplied to imaging unit 6a, in the section of length L1 from distal end portion 6 of the distal end of the endoscope to intermediate portion C1. Connection board 75 is connected to the end of first cable 81 on the relay board 71 side, and first cable 81 is detachably connected to relay board 71 via connection board 75.

Relay board 71 has an elongated shape such that the relay board is arranged within hard part 4, has, for example, a size of about 40 mm×7 mm, and has mounted thereon signal conversion IC 73 including a signal conversion circuit serving as an example of an imaging signal converter. Relay board 71 has connection board 75 connected to the other end of first cable 81 connected thereto by connector 85 and has one end of second cable 82 connected thereto by connector 86. Second cable 82 is inserted through hard part 4, and transmits the imaging signals after the conversion performed by the signal conversion circuit, and electric power and control signals to be supplied to imaging unit 6a and signal conversion IC 73, in the section of length L2 from intermediate portion C1 to base end portion C2. The other end of second cable 82 is connected to image output board 72.

In this way, a configuration is adopted in which relay board 71 is provided inside insert section 11, imaging signals are converted by the signal conversion circuit that constitutes the imaging signal converter mounted on relay board 71, and the imaging signals after the conversion are transmitted to image output board 72.

Image output board 72 is arranged in a space within grip section 2, and has image output IC 74 including the image output circuit mounted thereon. Image output board 72 has the other end of second cable 82 connected thereto by connector 87, and has one end of third cable 83 connected thereto by connector 88. Third cable 83 extends from grip section 2 of endoscope 1, and is connected to video processor 40.

As image pickup device 62 of imaging unit 6a, for example, a high-resolution image pickup device that can capture Full High Definition (Full-HD, 1080p or the like) is used. As the high-resolution image pickup device, an image pickup device, corresponding to Mobile Industry Processor Interface (MIPI) (registered trademark, the same applies below) Standards, which is a low-power element developed mainly for mobile device applications in order to suppress the amount of heat generation, is used. As for the power consumption of image pickup device 62, for example, the power consumption at the time of imaging is set to 110 mW or less. That is, in the present embodiment, an image pickup device corresponding to MIPI Standards in which a data transmission method for imaging signals is a low-amplitude differential transmission method is mounted as the low-power consumption image pickup device (low heat generation amount) that outputs high-resolution imaging signals.

For example, when imaging signals of the amount of data transmission of about 1.6 Gbps (the amount of data transmission of a frame rate of about 60 fps at a resolution of Full-HD and 1080p) are transmitted by a method based on the MIPI Standards, two-lane digital signals (MIPI signals) are output at 0.8 Gbps from image board 63 of imaging unit 6a. This is because the amount of transmissions based on the MIPI Standards cannot be secured in one lane of 1.6 Gbps. In this case, by setting the threshold level (threshold voltage: in this case, differential output voltage) of a digital output signal at the time of imaging in imaging unit 6a to, for example, 0.2 V or less, it is possible to suppress the power consumption for data transmission and to reduce heat generation of the distal end portion. However, a signal voltage and a signal transmission distance have a trade-off relationship, and when high-speed signal transmission in the order of Gbps is performed by an electrical signal, long-distance signal transmission at a low voltage becomes difficult. In the endoscope, when imaging signals are transmitted using the above MIPI signals, it is difficult to transmit signals with a length of about 700 mm from distal end portion 6 of insert section 11 to grip section 2 on the base end side.

This time, as a result of transmitting data signals at a differential output voltage of 0.2 V, it was confirmed that stable data transmission is possible up to 100 mm. It could be confirmed that the heat generation of the distal end portion is also suppressed to a temperature rise at which a burn or the like is not caused if the period of the temperature rise is short, even in a state where large-scale heat dissipation means is not included.

Thus, in the present embodiment, relay board 71 is provided at intermediate portion C1 of insert section 11 of which the possibility of directly touching an internal organ or the like within a human body is lower than the distal end portion, and signals are converted into signals by a second low-amplitude differential transmission method that allows relatively long-distance signal transmission, and signal transmission is performed from relay board 71 to image output board 72 of grip section 2. Here, in intermediate portion C1, the possibility of directly touching an internal organ or the like in a human body is low. Therefore, a differential output voltage for data signal transmission can be made high. Since not only the boards but sensors, lenses, mechanisms for performing tilting, and the like are configured in the distal end portion, it is difficult to secure the space for performing natural heat dissipation. However, the intermediate portion C1 also has relatively loose spatial restrictions, and members for performing natural heat dissipation are easily configured in the intermediate portion.

Due to the above reason, any kind of transmission method may be used as long as the transmission distance can be lengthened without being limited to the MIPI, which is the transmission standards of low power consumption, from intermediate portion C1.

Relay board 71 converts, for example, MIPI signals (0.8 Gbps×2 lanes) into digital signals (Serial Low Voltage Differential Signaling (SLVDS) signals) of 1.6 Gbps×1 lane of SLVDS Standards serving as a second low-amplitude differential transmission method, in signal conversion IC 73. Signal conversion IC 73 has a serial conversion circuit serving as the signal conversion circuit, and converts MIPI signals into low-amplitude differential signals (SLVDS signals) of serial transmission. In this case, the threshold level (threshold voltage: in this case, differential output voltage) of a digital output signal at the time of imaging in the signal conversion circuit that constitutes the imaging signals converter is set to, for example, 0.4 V or less.

This time, as a result of transmitting data signals at a differential output voltage of 0.4 V from intermediate portion C1, it was confirmed that stable data transmission is possible up to 600 mm. It could be confirmed that the heat generation of the intermediate portion C1 is also suppressed to a temperature rise at which a burn or the like is not caused if the period of the temperature rise is short, even in a state where large-scale heat dissipation means is not included.

For this reason, the threshold level of a digital output signal at the time of imaging in the image pickup device is smaller (the voltage is lower) than the threshold level thereof in the signal conversion circuit. That is, by making the threshold level in the section L1 lower than that in the section L2, the heat generation in the distal end portion of the insert section can be suppressed while achieving downsizing of the distal end portion of the insert section.

The transmission speed per lane of imaging signals output from image board 63 in the section L1 in which two-lane transmission is performed is lower than the transmission speed per lane in the section L2 in which one-lane transmission is performed. That is, by making the transmission speed in the section L1 lower than or equal to that in the section L2, the heat generation in the distal end portion of the insert section can be suppressed while achieving downsizing of the distal end portion of the insert section.

First cable 81 that connects image board 63 and relay board 71 is configured such that, for example, a plurality of thin-wire coaxial cables (AWG Line No. 46) are arranged in a flat belt shape, and transmits the MIPI signals (0.8 Gbps×2 lanes, first imaging signals) of differential signals, using two cables per one lane. First cable 81 transmits control signals and power source electric power between image board 63 and relay board 71 together with the first imaging signals based on the MIPI signals. Since first cable 81 is inserted through the hollow portion in bending portion 5 that is bent in a predetermined direction according to a bending operation, a cable material having excellent flexibility is used. In this case, first cable 81 transmits signals between image board 63 and relay board 71 at a distance of length L1 (about 100 mm). It is preferable that the distance between image board 63 and relay board 71, that is, a distance at which the MIPI signals before the conversion of the signals output from imaging unit 6a are transmitted by first cable 81 is, for example, 200 mm or less. In the present embodiment, as described above, length L1=about 100 mm is established.

First cable 81 may be any of single coaxial cables being discretely separated, ends of single coaxial cables being fixed together and bundled, coaxial cables being connected together in the shape of a flat cable, and the like. Otherwise, first cable 81 may be constituted of a combination of a plurality of thin-wire coaxial cables and a plurality of single-wire cables or a flexible flat cable (FFC), imaging signals may be transmitted by the thin-wire coaxial cables, and control signals and power source electric power may be transmitted by the single-wire cables or the FFC.

Second cable 82 that connects relay board 71 and image output board 72 is constituted of, for example, a combination of a Twinax cable and the FFC. In this case, in second cable 82, SLVDS signals (1.6 Gbps×1 lane, second imaging signals) are transmitted by the Twinax cable consisting of two sets of coaxial cables, each set having two coaxial cables, and control signals and power source electric power between relay board 71 and image output board 72 are transmitted by the FFC. Since second cable 82 is inserted through the hollow portion in hard part 4, flexibility like first cable 81 is not required, but a cable material having a certain degree of flexibility is used. In this case, second cable 82 transmits signals between relay board 71 and image output board 72 at a distance of length L2 (about 600 mm).

Image output board 72 converts SLVDS signals into transmission signals of Universal Serial Bus (USB) 3.0 Standards in image output IC 74. Image output IC 74 has a reverse serial conversion circuit and a USB signal conversion circuit as the image output circuit, and first performs reverse serial conversion of SLVDS signals to re-convert the converted SLVDS signals into MIPI signals, and then converts and outputs the re-converted MIPI signals as USB 3.0 signals. In image output board 72, SLVDS signals may be directly converted to USB 3.0 signals.

Third cable 83 that connects image output board 72 and video processor 40 is constituted of, for example, a signal cable corresponding to the USB 3.0 Standards, and transmits imaging signals of USB 3.0 signals, which are output from image output board 72, to video processor 40. Third cable 83 transmits control signals and power source electric power between grip section 2 of endoscope 1 and video processor 40, together with the imaging signals based on the USB 3.0 signals. In this case, third cable 83 transmits signals between endoscope 1 and video processor 40, for example, at a distance of about 2 m to 3 m. In image output board 72, instead of the USB 3.0 signals, conversion into signals of High-Definition Multimedia Interface (HDMI) (registered trademark: the same applies below) Standards may be performed or conversion into signals corresponding to other Standards or Specifications and the converted signals may be used.

Figure 6:
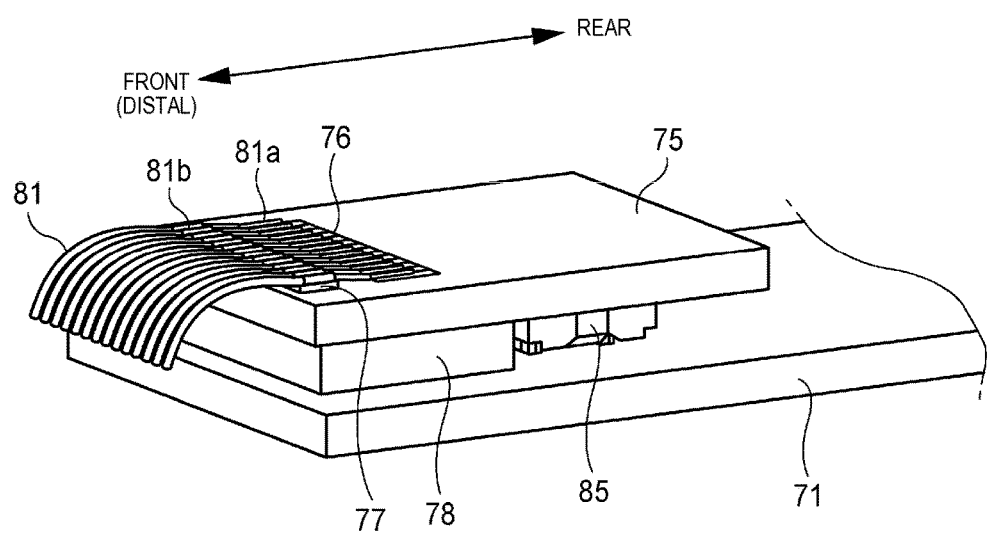
FIG. 6 is a view illustrating a specific configuration example of a relay board and a connection board.

Next, a detailed configuration of a connection of first cable 81 in relay board 71 will be described with reference to FIG. 6. FIG. 6 is a view illustrating a specific configuration example of relay board 71 and connection board 75.

Relay board 71 has a shape that is elongated in the longitudinal direction (in FIG. 6, the forward-rearward direction) of insert section 11, and has first cable 81 connected thereto via connection board 75. When first cable 81 is constituted of the plurality of thin-wire coaxial cables, each coaxial cable has core line (internal conductor) 81a at a central portion, and outside shield section (outer conductor) 81b. Pad 76 that becomes a cable connecting terminal and ground pattern 77 that becomes a ground connecting terminal are provided on one surface of connection board 75 so as to correspond to first cable 81. In this case, shield section 81b and core line 81a are electrically connected to and attached to ground pattern 77 of connection board 75 and pad 76, respectively, with solder or the like.

A ground conductor (not illustrated) conductively connected to ground pattern 77 and connector 85 attached so as to be conductively connected to pad 76 are provided on the other surface of connection board 75. Connection board 75 is electrically connected to relay board 71 by connector 85, and conductive material 78 that conductively connects the ground conductors of both boards is provided between connection board 75 and relay board 71. Conductive material 78 is constituted of, for example, a compressible and deformable conductive material, such as a conductive foamed material, is sandwiched between connection board 75 and relay board 71, and is connected to the ground conductor between the boards.

In this case, shield section 81b of first cable 81 is connected to the ground of relay board 71 via ground pattern 77 of connection board 75, the ground in connection board 75, and a ground terminal of connector 85. Moreover, a ground conductor of connection board 75 and a ground conductor of relay board 71 are connected to each other via conductive material 78. Conductive material 78 can ensure the grounding of connection board 75 and relay board 71, and can strengthen the grounding from first cable 81 to relay board 71. Since first cable 81 and relay board 71 can be detachably connected to each other with connector 85, assembility can be improved.

As described above, in the present embodiment, relay board 71 including the imaging signal converter that converts imaging signals output from imaging unit 6a is provided within insert section 11. Also, an image pickup device in which the data transmission method for imaging signals, such as the image pickup device corresponding to the MIPI Standards, is the low-amplitude differential transmission method, is used as image pickup device 62 to constitute low-power imaging unit 6a, and imaging signals are transmitted from imaging unit 6a to relay board 71 depending on low-voltage differential signals. Accordingly, since the high-resolution image pickup device can be mounted on the distal end portion of the insert section of the endoscope and imaging signals of a high frame rate can be transmitted, an image with high resolution and smooth movement can be captured. In this way, according to the present embodiment, the high-resolution image pickup device distal end mounting type endoscope can be realized.

By using the low-power consumption image pickup device as image pickup device 62, the heat generation in imaging unit 6a can be reduced, and the temperature rise of the distal end portion of the insert section can be suppressed. Since the imaging signals output from imaging unit 6a are low-amplitude and low-voltage signals, radiation noise to the outside can be suppressed in the distal end portion of the insert section that is restricted in shield performance in order to achieve downsizing.

First cable 81 is made of a cable material having excellent flexibility, and image board 63 and relay board 71 of imaging unit 6a are configured to be connected to each other with flexibility. For this reason, bending portion 5 can be freely bent, and the image pickup device distal end mounting type endoscope in which the visual field direction, position, or the like of imaging unit 6a of the distal end portion of the insert section, can be realized.

In the connection between first cable 81 and relay board 71, connection board 75 is provided, first cable 81 and relay board 71 are connected to each other by connector 85, and conductive material 78 that conductively connects the ground conductors of both the boards is provided between connection board 75 and relay board 71. Since the imaging signals, such as the MIPI signals transmitted by first cable 81, are the low-amplitude and low-voltage signals, the imaging signals tend to be influenced by the noise coming from the outside. However, the grounding between the boards can be ensured by conductive material 78, and grounding can be strengthened. Accordingly, the influence of extraneous noise can be reduced, and stable imaging signals can be output.

Although the various embodiments have been described above with reference to the drawings, the invention is not limited to these examples. It is apparent that a person skilled in the art may find various alternations and modifications within the scope of the appended claims, and it should be understood that they will naturally come under the technical scope of the present invention. The respective constituent elements in the above embodiments may be arbitrarily combined without departing from the scope of the invention.

What is claimed is:

1. An endoscope comprising:
    an insert section including a distal end portion, a bending portion, and a hard part, the bending portion being intermediate the distal end portion and the hard part;
    a low power imaging unit provided at the distal end portion of the insert section; and
    an imaging signal converter provided inside the insert section at the hard part, the imaging signal converter, which in operation, converts an imaging signal output from the imaging unit.

2. The endoscope of claim 1,
    wherein a data transmission method of an imaging signal transmitted from at least the imaging unit to the imaging signal converter is a low-amplitude differential transmission method.

3. The endoscope of claim 2,
    wherein a transmission speed per lane of a first imaging signal transmitted from the imaging unit to the imaging signal converter is lower than or equal to a transmission speed per lane of a second imaging signal after the signal conversion using the imaging signal converter.

4. The endoscope of claim 1,
    wherein the imaging unit includes an image pickup device, power consumption by the image pickup device at the time of imaging being 110 mw or less.

5. The endoscope of claim 1,
    wherein a threshold level of a digital output signal at the time of imaging in the imaging unit is equal to or less than 0.2 V, and
    wherein a threshold level of a digital output signal at the time of imaging in the imaging signal converter is equal to or less than 0.4 V.

6. The endoscope of claim 2,
    wherein a distance which an MIPI signal is transmitted before the conversion of the imaging signal output from the imaging unit is 200 mm or less.

7. The endoscope of claim 1, wherein the bending portion is intermediate the low power imaging unit and the imaging signal converter.

* * * * *